United States Patent [19]

Marsoner et al.

[11] Patent Number: 4,755,667

[45] Date of Patent: Jul. 5, 1988

[54] SENSOR ELEMENT FOR DETERMINATION OF CONCENTRATION OF SUBSTANCES

[75] Inventors: Hermann Marsoner, Steinberg; Hellfried Karpf; Alfred Leitner, both of Graz, all of Austria

[73] Assignee: AVL AG, Schaffhausen, Switzerland

[21] Appl. No.: 40,628

[22] Filed: Apr. 17, 1987

[30] Foreign Application Priority Data

Oct. 10, 1986 [AT] Austria .................................. 2706/86

[51] Int. Cl.⁴ ...................... G01N 21/00; G01N 21/64
[52] U.S. Cl. .................................. 250/227; 250/461.1; 356/417
[58] Field of Search ............ 250/574, 576, 227, 461.1, 250/484.1; 356/338–343, 317, 318, 417, 39

[56] References Cited

U.S. PATENT DOCUMENTS 3,604,927 9/1971 Hirschfeld ............................ 356/317
3,962,581 6/1976 Zimmerman ......................... 356/338
4,269,516 5/1981 Libbers et al. ......................... 356/39

FOREIGN PATENT DOCUMENTS 2508637 11/1979 Fed. Rep. of Germany .
106086 5/1974 German Democratic Rep. .

Primary Examiner—Edward P. Westin
Attorney, Agent, or Firm—Watson, Cole, Grindle & Watson

[57] ABSTRACT

A sensor element for use in determining the concentrations of substances contained in gaseous and liquid samples includes a carrier layer and an indicator layer containing one or more indicator substances whose optical properties change depending on the concentration of the substances to be measured, the carrier layer being provided with at least one photosensitive element with electrical contacts in planar arrangement, the indicator layer acting as a waveguide for excitation radiation coupled therein by an optical element.

18 Claims, 3 Drawing Sheets

SENSOR ELEMENT FOR DETERMINATION OF CONCENTRATION OF SUBSTANCES

BACKGROUND OF THE INVENTION

This invention relates to a sensor element for determining the concentrations of substances contained in gaseous and liquid samples, and which comprises a carrier layer and an indicator layer with one or more indicator substances whose optical properties, or at least one of them, will change upon interaction with the substance to be measured, depending on the latter's concentration.

DESCRIPTION OF THE PRIOR ART

Optical sensors for determining the concentrations of substances by means of indicators, in particular sensors based on a change in the fluorescent properties of the indicator upo interaction with the substance to be measured, have been state of the art for a considerable time. For example, DE-PS No. 25 08 637 presents a sensor element of the above type in which a thin layer of the indicator solution is deposited on a suitable carrier material and the indicator solution is covered by a membrane which is permeable to the substance to be measured. On the carrier side of this configuration a complex lighting and photometric assembly is located, comprising a number of optical elements both in the path of the excitation light and in that of the fluorescent light.

In an arrangement described in DD-PS No. 106 086 the fluorescent indicator is contained in a layer extending over a measuring chamber and a reference measuring chamber; in this instance, however, the indicator layer is shielded against the medium to be measured in the area of the reference measuring chamber. From the difference in fluorescence intensities obtained in the measuring chamber and in the reference measuring chamber, respectively, the concentration of the substance to be measured is directly inferred. The fluorescent light from the measuring chambers is fed into a photoelectric converter each by means of optical fiber-guides.

The above sensors thus usually consist of a reaction space which may be configured as a thin layer and which contains the indicator substance in a given geometrical configuration. From a position facing away from the sample, light of a given wavelength is transmitted to the indicator layer via a light source and suitable optical devices, for instance lightguides or optical fibers. The fluorescent light which is diffusely reflected and emitted in all directions by the indicator layer is carried to a photodetector from the same side of the reaction space or the indicator layer, again with the use of suitable optical devices and filters. The side of the reaction space facing away from the optical devices is brought into contact with the gaseous or liquid sample, the substance to be measured usually entering the reaction space by diffusion and interacting with the indicator molecules of the indicator substance, whose optical properties, above all absorption and fluorescent properties, will change thereupon, depending on the concentration of the substance. There is a functional relationship between the degree and character of this change and the particle concentration to be measured.

This size of such configurations is determined by the size of the sensor itself on the one hand, and by the geometry and size of the optical devices required for picking up the fluorescent and/or reflected radiation on the other hand.

SUMMARY OF THE INVENTION

It is essential for such sensors, for instance if they are designed for use in microanalysis, that they should be made extremely small and simple to manufacture, this task being complicated by the fact that in conventional sensors the excitation light is used inefficiently, as most of the excitation radiation passes the sensor layer without interacting with the indicator substances.

In the present invention the above aims are achieved by providing the carrier layer with one or more photosensitive elements including their electrical contacts in planar arrangement, and by configuring the indicator layer containing the indicator substance as a waveguide for the excitation radiation, which can be coupled into the indicator layer by means of an optical element, and by establishing optical contact between the indicator substance excited by the excitation light and the photosensitive element(s). All layers of the sensor, including the indicator layer, are produced by standard microelectronic techniques, such as evaporation coating, sputtering, spinning, etc., the required extreme miniaturization of the entire sensor unit being achieved by directly integrating the photosensitive elements and their electrical contacts into the carrier layer or into a separate thin-film substrate of the sensor element. In this way the fluorescent or reflected radiation to be measured is picked up in the sensor element itself, thereby rendering superfluous all photometric devices formerly required outside the sensor element. The measuring signals are directly fed into an electronic display/evaluation unit via electrical leads.

According to the invention the sensor layer is preferably used as a waveguide for the excitation light at the same time. The passage of the excitation light through this layer is not normal to the boundary layer—as would be the case in conventional sensors—but parallel to the surface of the extremely thin sensor layer, which will permit much better utilization of the excitation radiation. Coupling of the excitation light into the thin indicator layer is achieved by means of a suitable optical element.

Providing the electrical contacts of the optoelectrical elements of the sensor does not represent any restriction in terms of the invention, as the respective contact paths can also be established by known microelectronic techniques.

A sensor element as described by the invention may be provided with various indicator layers that have been optimized for special tasks, and at least some of them can be deposited by microelectronic thin-film techniques.

A further development of the invention provides that the optical element be a coupling prism attached to the indicator layer acting as a waveguide. A coupling prism is a body transparent to the excitation radiation, which is bonded to the waveguide layer after depositing. It will permit the coupling of larger amounts of light into very thin waveguide layers.

Another variant of the invention provides that the optical element be a so-called grating coupler which is preferably attached to the side of the waveguide indicator layer facing away from the sample. A grating coupler is considered a suitable alternative to the above coupling prism; it may also be produced by thin-layer techniques, which will further simplify manufacture of the sensor elements.

In a preferred form of the invention the photosensitive element is configured as an annular diode and the grating coupler situated on the indicator layer in the inner circular area of the diode. Such a sensor element can be made for instance by etching an annular diode structure out of a wafer already carrying all the layers of a photodiode (as a photosensitive element). The other layers including the grating coupler are then deposited in the inner circular area of the diode by sputtering or spinning techniques.

Yet another variant of the invention provides that at least two photodiodes be placed symmetrically, i.e., one on either side of the grating coupler, to act as photosensitive elements. It is also possible to choose a non-circular structure, which will render manufacture of the grating coupler easier and cheaper, in addition to permitting the use of conventional rectangular or square photodiodes.

In a further development of the invention the optical element is connected, at least indirectly, to the end of a lightguide, particularly a single optical fiber, possibly with an excitation filter situated between the end of the fiber and the optical element. In a sensor with an annular diode for example, the end of a lightguide may be introduced into the inner circular area of the diode. Via the grating coupler placed in this area the excitation light is deflected and radially coupled into the sensor layer configured as a waveguide. By suitably dimensioning the lightguide, e.g., a single fiber, and the thickness of the sensor layer, and by selecting appropriate refractive indices, the excitation light can be utilized most effectively. It will also be possible, of course, to provide a filter layer between the end of the lightguide and the optical element, which will filter out of the excitation radiation the optimum wavelength for excitation.

The excitation light can be utilized more fully if the ratio of the refractive indices of core and cladding of the optical fiber differs only slightly from that of the refractive indices of indicator layer and sample.

In a further development of the basic idea of the invention a light-emitting source is placed in the area of the grating coupler, possibly including an excitation filter between grating coupler and light-emitting source. The additional integration of light-emitting sources, e.g., LEDs, will allow further miniaturization of the entire sensor unit. Preferably, this sensor element is provided with electrical contacts only, as all optical devices outside of the sensor element are eliminated. This sensor is easy to mass-produce, and standard manufacturing techniques of semi-conductor technology may be used for the entire sensor element.

For better separation of the fluorescence radiation to be measured from the excitation radiation, in a further development of the invention the photosensitive elements are covered by a filter layer, preferably an interference filter. Again, all excitation and emission filters used can be produced and deposited by standard microelectronic thin-film techniques.

Another variant of the invention provides a transparent layer (channel plate) between the photosensitive elements and the indicator layer, whose angle of acceptance will prevent the transport of excitation radiation to the photosensitive elements, and different indicator substances are used in individual areas of the indicator layer corresponding to certain photosensitive elements. This permits simultaneous measuring of several concentrations of substances contained in gaseous or liquid samples, provided that different indicator substances with specific responses to individual materials are used in the individual areas. Depositing different indicator substances in areas of the indicator layer of a few hundred micrometers diameter only is achieved by microscreen printing or evaporation techniques. For this purpose thin layers of material are deposited by microscreen printing techniques or similar processes on certain zones defined by a mask, which in turn is produced by a photographic process.

Finally, the invention proposes that the indicator layer be provided in a known manner with a cover layer on the side next to the sample. This cover layer may consist of a polymer film into which pigments have been incorporated, thus barring the excitation light and the fluorescent light from entering the sample chamber, and preventing undesired reflexions or fluorescences in this area. A suitable cover layer will also help protect the indicator layer from macro-molecular components of the sample which would influence the measuring result. If a suitable refractive index is selected for the cover layer the waveguide function of the indicator layer will be enhanced. It is furthermore possible to deposit a cover layer with selective properties such that the diffusion of the substances to be measured into the indicator layer is encouraged.

In view of the microelectronic techniques employed for manufacture, another advantage of such microsensors is that electronic circuits are integrated into the carrier layer which are intended for amplification of the electric signals of the photosensitive elements and/or for control of the brightness of the radiation generated by the light-emitting sources. According to the invention even further integration is achieved by providing the carrier layer with highly integrated electronic circuits for signal evaluation tasks. For example, separate circuits can be assigned to individual photosensitive elements with filter layers of different pass bands, which will permit multiwavelength analysis in the sensor element itself.

DESCRIPTION OF THE DRAWINGS

The invention will now be further illustrated with reference to the accompanying drawings, in which.

DETAILED DECRIPTION OF THE PREFERRED EMBODIMENTS

Figure 1:
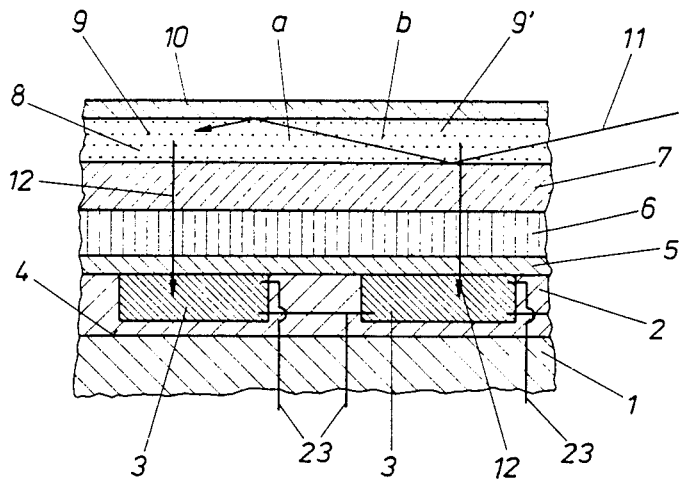
FIG. 1 is a schematic view of a section through a sensor element according to the invention.

FIG. 1 shows a sensor element according to the invention, comprising photosensitive elements 3 which are embedded in a thin-film substrate 2 on a suitable carrier layer 1, and which are integrated into this substrate 2 in planar arrangement parallel to the surface 4 of the carrier layer 1. The photosensitive elements 3 are covered by an optical filter layer 5, i.e., preferably an interference filter, which is deposited by suitable microelectronic techniques. It is also possible, however, to place the photosensitive elements 3 directly on the carrier layer 1 and to coat them by a filter layer. On top of the filter layer 5 there is a transparent layer or channel plate 6, whose angle of acceptance is so small as to admit only light whose direction of incidence is normal to the surface of the channel plate. On top of this transparent layer 6 there is a layer of glass 7 with a low refractive index $n_1$, functioning as a boundary layer for the indicator layer 8 acting as a waveguide. The indicator layer 8, with a refractive index $n_2$ greater than $n_1$, contains an indicator substance 9, several different indicator substances 9, 9' being conceivable, which may be contained in individual areas a, b of the indicator layer, corresponding to individual photosensitive elements 3. On the side next to the sample the sensor element has a cover layer 10 whose refractive index $n_3$ again is smaller than the refractive index $n_2$ of the indicator layer 8. The cover layer 10 may be omitted, provided that the adjoining sample medium has an appropriate refractive index permitting the indicator layer 8 to act as a waveguide.

Figure 2:
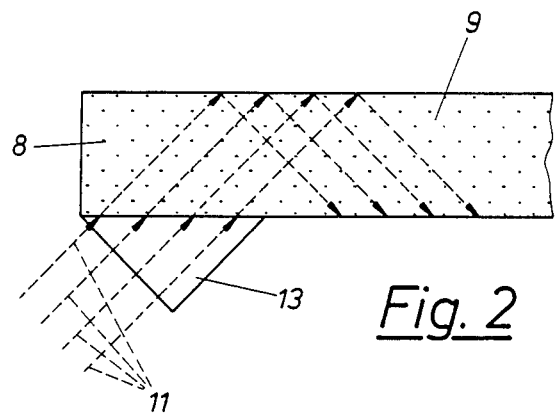
FIG. 2 is an enlarged view of the indicator layer of the sensor element of FIG. 1 and showing a coupling prism bonded thereto.

For excitation of the indicator substances 9, 9' the excitation light 11 is coupled from the side into the indicator layer 8 whose thickness is only a few micrometers, in which it is guided by total reflection due to the ratio of the refractive indices of the indicator layer 8 on the one hand and the adjoining glass layer 7 or the cover layer 10 on the other hand, illuminating the entire indicator layer. In order to couple the excitation light 11 into the extremely thin indicator layer 8, an optical element as shown in FIG. 2 is required, for example a coupling prism 13, which may be bonded to the waveguide layer after depositing. Only the use of such a coupling prism will enable larger quantities of light to be entered into the extremely thin indicator layer. The fluorescence radiation 12 generated in the indicator layer 8, which is emitted in all directions, will reach the respective photosensitive elements 3 via the glass layer 7 and the channel plate 6, after having been filtered by the filter layer 5. The channel plate 6 will prevent the transport of excitation light to the photosensitive elements 3 while permitting th assignment of different photosensitive elements 3 to certain areas a, b.

As the channel plate or transparent layer 6 separates the exciting light 11 from the fluorescent light 12 due to its angle of acceptance, the variant presented in FIG. 1 may be modified by omitting the filter layer 5 covering the photosensitive elements 3. Scattered light occurring as a consequence of impurities or other anisotropies of the indicator layer 8 or its boundary layers, has a constant level and can be compensated for by a reference measurement.

Figure 3:
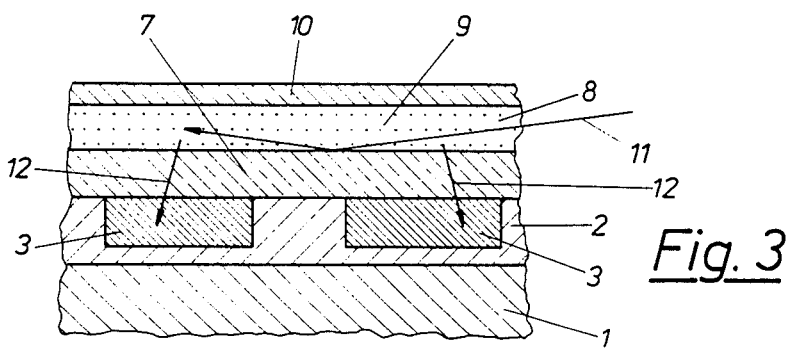
FIG. 3 is a simplified variant of the sensor element according to FIG. 1.

As is shown in the simplified variant of FIG. 3, both the channel plate and the filter layer 5 covering the photosensitive elements may be omitted. The excitation light 11 is transmitted in the light waveguide constituted by the glass layer 7, indicator layer 8 and cover layer 10, exciting the indicator substances 9 contained in the indicator layer 8. The photodiodes will only pick up the fluorescent light 12 and scattered light, which latter may be compensated for by a reference measurement, as mentioned above.

The electrical contacts of the photosensitive elements 3 are not shown in detail in these Figures, as they are integrated into the carrier layer 1, or rather in the substrate 2, with the use of standard microelectronic techniques; only the electrical contact pins and wires 23 leaving the sensor elements through the carrier layer 1 can be seen in FIG. 1 and FIG. 4 to be discussed below, which pins and wires may also be located in other places of the sensor element according to the present invention.

In all other embodiments of the invention identical parts have identical reference numbers.

Figure 4:
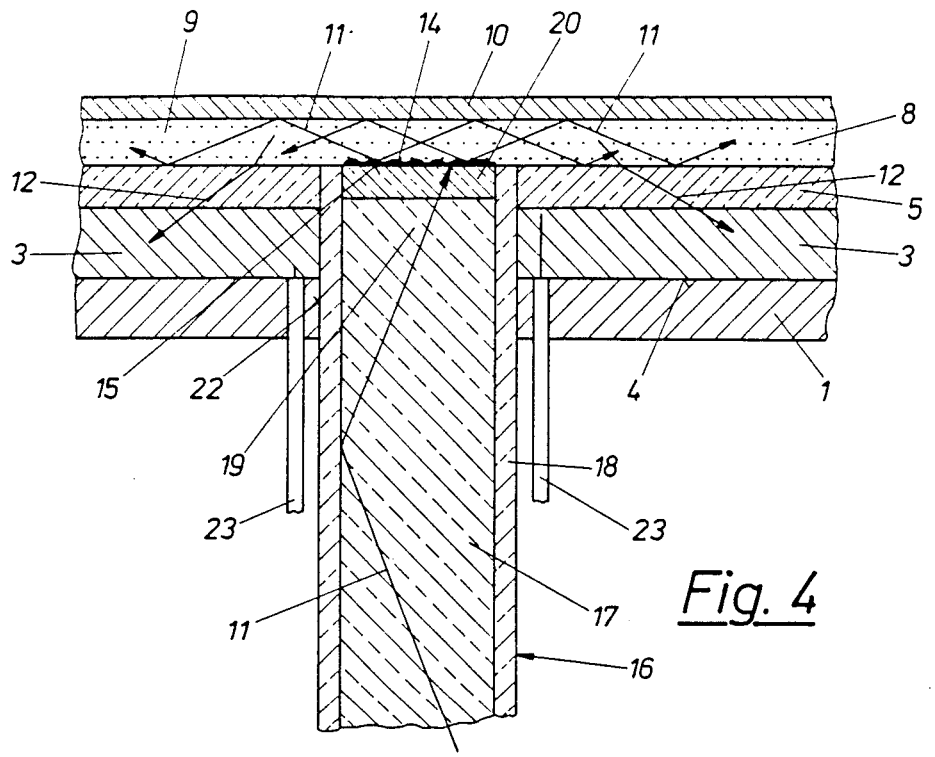
FIG. 4 is a section through another variant.

For manufacture of a sensor element as shown in FIG. 4 a wafer may be used as a starting material which is already provided with all the layers of a photodiode (photosensitive element 3). By means of suitable microelectronic techniques a filter layer 5, an indicator layer 8 and, possibly, a cover layer 10 are deposited on this wafer. The filter layer 5 has a smaller refractive index than the indicator layer 8 and will therefore serve as a boundary layer for the indicator layer 8 acting as a waveguide. If the cover layer 10 is omitted, the sample medium must have an appropriate refractive index, as has been described above. A recess 22 on the side of the sensor element facing away from the sample, which extends as far as to the indicator layer 8, contains the end 19 of a lightguide 16, preferably a single fiber. On the side 15 of the waveguide indicator layer 8 facing away from the sample there is a grating coupler 14 which will deflect the excitation light 11 transmitted through the lightguide and couple it into the indicator layer 8. The fluorescent light 12 emitted in all directions enters the photosensitive element 3; or rather the annular photodiode with its contact pins and wires 23, through the filter layer 5. Particularly favorable conditions for excitation will arise if the ratio of the refractive indices of core 17 and cladding 18 of the lightguide 16 differs only slightly from that of the refractive indices of indicator layer 8 and cover layer 10 or the sample. It will also be possible, of course, to provide an excitation filter 20 between the end 19 of the lightguide 16 and the grating coupler 14.

Figure 5:
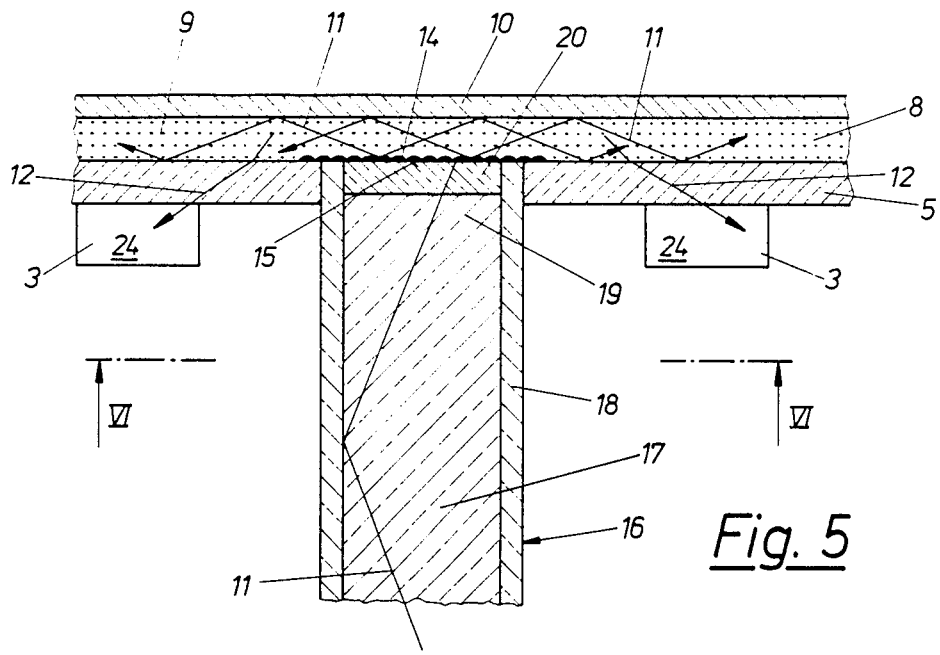
FIG. 5 is a variant of the sensor element presented in FIG. 4.
Figure 6:
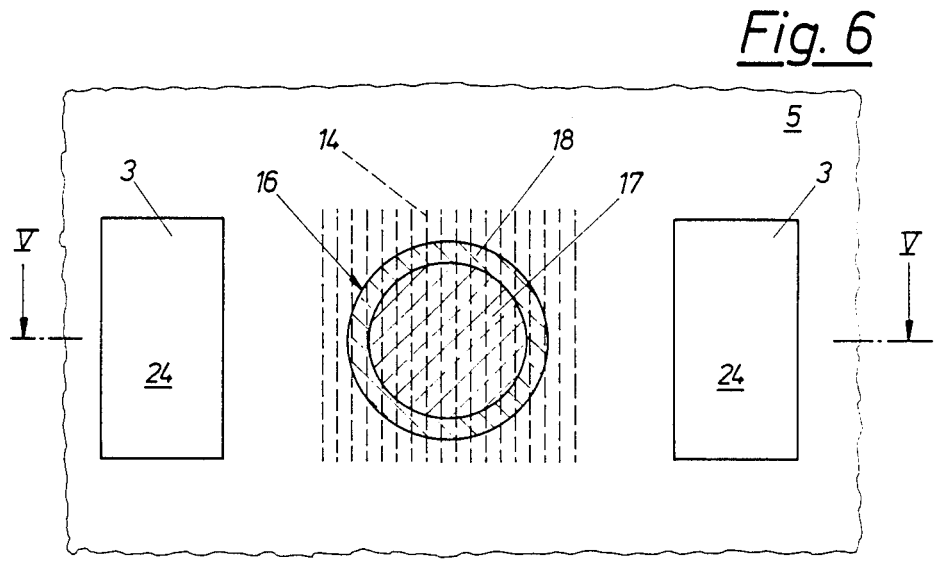
FIG. 6 is a section along line VI—VI in FIG. 5.

As is shown in FIGS. 5 and 6, a rectangular or square arrangement may be used for grating coupler and photosensitive elements 3, which will make manufacture of the grating coupler 14 simpler and cheaper. As photosensitive elements 3 commercially available, photodiodes 24 of a rectangular or square shape may be used, which are directly attached to the filter layer 5.

Figure 7:
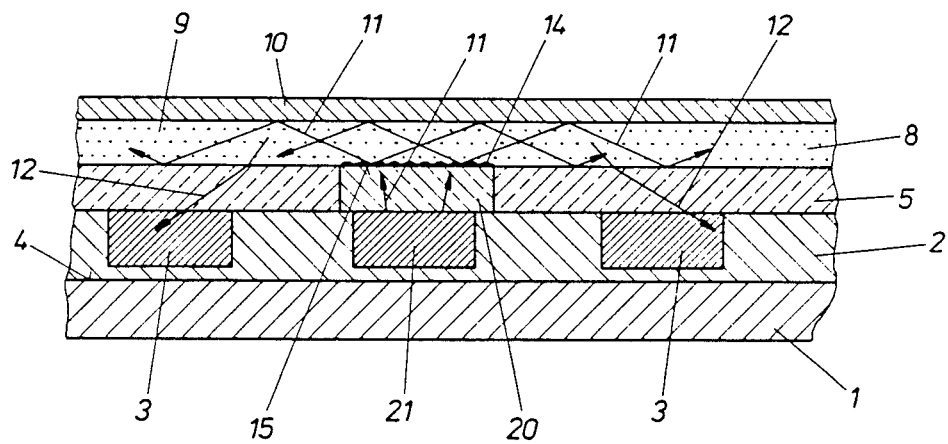
FIG. 7 is yet another variant of a sensor element according to the invention.

FIG. 7 presents a variant of the sensor element shown in FIG. 4, which differs from the latter only by the use of a light-emitting source 21 in the area of the grating coupler 14, with all opto-electrical elements including their contacts being integrated in a substrate 2. Electrical leads towards the light-emitting source, e.g., a LED, or out of the diodes are not shown here.

We claim:

1. A sensor element for determining the concentrations of substances contained in gaseous and liquid samples, comprising a carrier layer and an indicator layer, comprising one or more indicator substances, at least one of the optical properties of said indicator substances will change upon interaction with said substance to be measured, depending on the concentration of said substance, wherein said carrier layer is provided with at least one photosensitive element and electrical contacts of said photosensitive element in planar arrangement, wherein said indicator layer containing said indicator substance is acting as a waveguide for excitation radiation, said excitation radiation can be coupled into said indicator layer by means of an optical element, and wherein said indicator substance excited by said excitation radiation is in optical contact with said photosensitive element.

2. A sensor element according to claim 1, wherein said optical element is a coupling prism which is attached to said indicator layer acting as said waveguide.

3. A sensor element according to claim 1, wherein said optical element is a grating coupler which is attached to a side of said indicator layer facing away from said sample.

4. A sensor element according to claim 3, wherein said photosensitive element is configured as an annular diode having an inner circular area, and wherein said grating coupler is situated on said indicator layer in said inner circular area of said diode.

5. A sensor element according to claim 3, wherein two or more photodiodes are placed symmetrically, i.e., at least one on either side of said grating coupler, to act as said photosensitive elements.

6. A sensor element according to claim 2, wherein said optical element is connected, at least indirectly, to the end of a lightguide, having an excitation filter situated between said end of said lightguide and said optical element.

7. A sensor element according to claim 3, wherein said optical element is connected, at least indirectly, to the end of a lightguide, having an excitation filter situated between said end of said lightguide and said optical element.

8. A sensor element according to claims 6 or 7, wherein said lightguide comprising a core and a cladding, said core, said cladding, said indicator layer and said sample having refractive indices and wherein the ratio of said refractive indices of said core and said cladding differs only slightly from the ratio of said refractive indices of said indicator layer and said sample.

9. A sensor element according to any of claims 3 to 5, wherein a light-emitting source is provided facing said grating coupler including an excitation filter situated between grating coupler and light-emitting source.

10. A sensor element according to claim 1, wherein said photosensitive elements are covered by a filter layer, in particular an interference filter.

11. A sensor element according to claim 10, wherein said filter layer is an interference filter.

12. A sensor element according to claim 1, wherein a transparent layer or channel plate, having an angle of acceptance, is added between said photosensitive elements and said indicator layer, said angle of acceptance prevents transport of said excitation radiation to said photosensitive elements.

13. A sensor element according to claim 12, wherein different indicator substances are used in individual areas of said indicator layer corresponding to certain of said photosensitive elements.

14. A sensor element according to claim 1, wherein said indicator layer is provided with a cover layer on the side facing said sample.

15. A sensor element according to claim 9, wherein additional electronic circuits are integrated into said carrier layer, said electronic circuits are used for amplifying electric signals of said photosensitive elements and/or for control of the brightness of radiation generated by said light-emitting sources.

16. A sensor element according to claim 9, wherein said carrier layer is provided with highly integrated electronic circuits for signal evaluation tasks.

17. A sensor element according to claim 1, wherein additional electronic circuits are integrated into said carrier layer, said electronic circuits are used for amplifying electric signals of said photosensitive elements and/or for control of the brightness of radiation generated by said light-emitting sources.

18. A sensor element according to claim 1, wherein said carrier layer is provided with highly integrated electronic circuits for signal evaluation tasks.

* * * * *